United States Patent
Fahl et al.

(10) Patent No.: US 9,216,147 B2
(45) Date of Patent: Dec. 22, 2015

(54) MILD COSMETIC CLEANSING COMPOSITION

(71) Applicant: Henkel AG & Co. KGaA, Duesseldorf (DE)

(72) Inventors: Madlen Fahl, Tangendorf (DE); Dirk Hentrich, Hamburg (DE); Thomas Schroeder, Hamburg (DE); Jens Meyer, Wedel (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/256,499

(22) Filed: Apr. 18, 2014

(65) Prior Publication Data

US 2014/0228268 A1  Aug. 14, 2014

Related U.S. Application Data

(63) Continuation of application No. PCT/EP2012/070249, filed on Oct. 12, 2012.

(30) Foreign Application Priority Data

Oct. 20, 2011  (DE) .......... 10 2011 084 888

(51) Int. Cl.
| | | |
|---|---|---|
| *A61K 8/46* | (2006.01) | |
| *A61Q 5/02* | (2006.01) | |
| *A61Q 19/10* | (2006.01) | |
| *A61K 8/44* | (2006.01) | |
| *A61K 8/60* | (2006.01) | |
| *A61K 8/37* | (2006.01) | |
| *A61K 8/41* | (2006.01) | |
| *A61K 8/73* | (2006.01) | |

(52) U.S. Cl.
CPC . *A61K 8/466* (2013.01); *A61K 8/37* (2013.01); *A61K 8/41* (2013.01); *A61K 8/442* (2013.01); *A61K 8/602* (2013.01); *A61K 8/73* (2013.01); *A61Q 5/02* (2013.01); *A61Q 19/10* (2013.01)

(58) Field of Classification Search
None
See application file for complete search history.

(56) References Cited

FOREIGN PATENT DOCUMENTS

| | | |
|---|---|---|
| EP | 0569028 A2 | 11/1993 |
| EP | 1674132 A1 | 6/2006 |
| EP | 2468842 A1 | 6/2012 |
| WO | 2009/063250 A2 | 5/2009 |
| WO | 2009/135007 A1 | 11/2009 |
| WO | 2011/007174 A2 | 1/2011 |
| WO | 2011/015857 A2 | 2/2011 |
| WO | 2011/015858 A2 | 2/2011 |

OTHER PUBLICATIONS

PCT International Search Report (PCT/EP2012/070249) dated May 8, 2013.

*Primary Examiner* — Necholus Ogden, Jr.
(74) *Attorney, Agent, or Firm* — David K. Benson

(57) ABSTRACT

A mild cosmetic cleansing agent includes in a suitable carrier a) 1 to 6 wt. % of at least one anionic surfactant of the following formula (I),

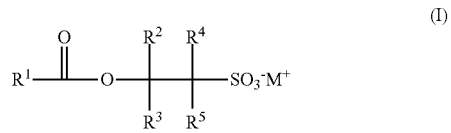

in which $R^1$ denotes a linear or branched, saturated or unsaturated alkyl residue having 6 to 30 carbon atoms, at least one of the residues $R^2$ to $R^5$ denotes a $C_1$-$C_4$ alkyl residue, and the other residues independently of one another denote a hydrogen atom or a $C_1$-$C_4$ alkyl residue, and $M^+$ denotes an ammonium, alkanolammonium or metal cation, b) 2 to 10 wt. % of at least one amphoteric and/or zwitterionic surfactant and c) 0.5 to 10 wt. % of at least one non-ionic surfactant and/or at least one non-ionic emulsifier, selected from at least one of the following groups of alkyl (oligo)glycosides, amine oxides and/or glycerol mono- and/or di($C_6$-$C_{24}$) carboxylic acid esters, wherein the stated amounts relate to the total weight.

12 Claims, No Drawings

MILD COSMETIC CLEANSING COMPOSITION

FIELD OF THE INVENTION

The present invention generally relates to cosmetics, and more particularly relates to mild cleansing agents including a special mixture of surfactants.

BACKGROUND OF THE INVENTION

Cosmetic cleansing agents, such as for example hair shampoos, are based on conventional anionic, amphoteric, zwitterionic, non-ionic and/or cationic surfactants.

Owing to their outstanding cleansing and foaming ability, anionic surfactants, optionally mixed with small amounts of co-surfactants, are predominantly used.

Typical anionic surfactants, which are used in a large number of commercially available shampoos, are alkyl sulfates or alkyl ether sulfates.

Alkyl ether sulfates are conventionally preferred as they are milder and have an excellent foaming ability.

When formulating especially mild cleansing compositions for use on sensitive parts of the skin (such as facial skin for example) or for use on babies' skin, alkyl ether sulfates are not always satisfactory, as they have too high an irritation potential for these applications.

Thus countless attempts have been made in the past to find especially mild surfactant blends that have sufficiently large amounts of foam and sufficiently high foam qualities and that have little or no irritation potential on the skin and/or mucous membranes.

The application WO 92/084440 discloses mild surfactant blends having outstanding foam properties, which include a mixture of acyl isethionates, zwitterionic surfactants and alkyl ether sulfates.

WO 11/015857 discloses cleansing compositions having low irritation potential and including novel $C_{5-30}$ alkoyl-alkyl isethionates and amphoteric surfactants in a weight ratio from 4:1 to 1:4. The mild cleansing agents are suitable for use as a baby shampoo.

The disadvantage of many mild skin and hair cleansing agents is that the improved skin compatibility thereof often comes at the expense of the texture of the cleansing agents.

It has moreover been observed that the care properties of mild cleansing agents (in particular on the hair) are not always satisfactory.

In practice, silicones and/or ethoxylated components have often been added to mild surfactant blends to improve the care properties of the agents, which from an application-related perspective is not desirable in sensitive products and/or baby care products.

The object of the present invention was to produce particularly mild cosmetic cleansing agents that are readily tolerated by the skin and mucous membranes.

The cleansing agents should have a user-friendly texture and should be free-flowing.

Furthermore, the care properties of mild cleansing compositions should be improved without an addition of ethoxylated components and/or an addition of silicones. In particular, mild cosmetic cleansing agents that satisfy the aforementioned requirements even at relatively low pH values should be developed.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A mild cosmetic cleansing agent, including in a suitable carrier a) 1 to 6 wt. % of at least one anionic surfactant of the following formula (I), $$R^1-\overset{O}{\overset{\|}{C}}-O-\overset{R^2}{\underset{R^3}{\overset{|}{C}}}-\overset{R^4}{\underset{R^5}{\overset{|}{C}}}-SO_3^-M^+ \quad (I)$$

in which $R^1$ denotes a linear or branched, saturated or unsaturated alkyl residue having 6 to 30 carbon atoms; at least one of the residues $R^2$ to $R^5$ denotes a $C_1$-$C_4$ alkyl residue, and the other residues independently of one another denote a hydrogen atom or a $C_1$-$C_4$ alkyl residue; and $M^+$ denotes an ammonium, alkanolammonium or metal cation; b) 2 to 10 wt. % of at least one amphoteric and/or zwitterionic surfactant; and c) 0.5 to 10 wt. % of at least one non-ionic surfactant and/or at least one non-ionic emulsifier, selected from at least one of the following groups of alkyl (oligo)glycosides, amine oxides and/or glycerol mono- and/or di($C_6$-$C_{24}$) carboxylic acid esters, wherein the stated amounts relate to the total weight of the cleansing agent.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The invention provides a mild cosmetic cleansing agent including in a suitable carrier
a) 1 to 6 wt. % of at least one anionic surfactant of the following formula (I), $$R^1-\overset{O}{\overset{\|}{C}}-O-\overset{R^2}{\underset{R^3}{\overset{|}{C}}}-\overset{R^4}{\underset{R^5}{\overset{|}{C}}}-SO_3^-M^+ \quad (I)$$

in which
$R^1$ denotes a linear or branched, saturated or unsaturated alkyl residue having 6 to 30 carbon atoms,
at least one of the residues $R^2$ to $R^5$ denotes a $C_1$-$C_4$ alkyl residue, and the other residues independently of one another denote a hydrogen atom or a $C_1$-$C_4$ alkyl residue, and
$M^+$ denotes an ammonium, alkanolammonium or metal cation,
b) 2 to 10 wt. % of at least one amphoteric and/or zwitterionic surfactant and
c) 0.5 to 10 wt. % of at least one non-ionic surfactant and/or at least one non-ionic emulsifier, which is selected from at least one of the following groups of
alkyl (oligo)glycosides,
amine oxides and/or
glycerol mono- and/or di($C_6$-$C_{24}$) carboxylic acid esters,
wherein the stated amounts relate to the total weight of the cleansing agent.

A suitable carrier is understood to be preferably an aqueous or aqueous-alcoholic carrier.

The carrier preferably includes at least 50 wt. %, more preferably at least 60 wt. % and more preferably at least 70 wt. % water.

The cosmetic carrier can moreover include 0.01 to 40 wt. %, preferably 0.05 to 35 wt. % and in particular 0.1 to 30 wt. % of at least one alcohol, which can be selected from ethanol, 1-propanol, 2-propanol, isopropanol, glycerol, diglycerol, triglycerol, 1-butanol, 2-butanol, 1,2-butanediol, 1,3-butanediol, 1-pentanol, 2-pentanol, 1-hexanol, 2-hexanol, sorbitol, sorbitan, benzyl alcohol, phenoxyethanol or mixtures of said alcohols.

The water-soluble alcohols are preferred.

Ethanol, 1-propanol, 2-propanol, isopropanol, glycerol, benzyl alcohol and/or phenoxyethanol and mixtures of said alcohols are more preferred. Glycerol is preferred in particular.

In order to achieve optimum mildness and care properties, cleansing agents according to the invention include the surfactants/emulsifiers a), b) and c) in a weight ratio of (1-2):(2-5):(1-3).

Preferred anionic surfactants of the aforementioned formula (I) have a linear or branched, saturated or unsaturated alkyl residue having 8 to 18 carbon atoms as the residue $R^1$. The residue $R^1$ more preferably denotes a $C_8$, $C_{10}$, $C_{12}$, $C_{14}$, $C_{16}$ residue or mixtures of these fatty acid residues, such as are obtained when the fatty acid(s) is/are derived from natural oils such as for example coconut oil.

In further preferred anionic surfactants of the aforementioned formula (I), the residues $R^2$ to $R^5$ can in each case denote a methyl, ethyl, n-propyl, n-butyl or 2-butyl group.

At least one of the residues $R^2$ to $R^5$ preferably denotes a methyl, ethyl or n-propyl group, in particular a methyl group.

In a more preferred embodiment only one of the residues $R^2$ to $R^5$ denotes a $C_1$-$C_4$ alkyl group—in particular a methyl group—while the other residues each denote a hydrogen atom.

It is also possible in principle for the anionic surfactant according to formula (I) to include a mixture of isomers including both components having for example a $C_1$-$C_4$ alkyl group—in particular a methyl group—as the residue $R^2$ and a hydrogen atom in each case as the residues $R^3$ to $R^5$, and components having for example a $C_1$-$C_4$ alkyl group—in particular a methyl group—as the residue $R^5$ and a hydrogen atom in each case as the residues $R^2$ to $R^4$.

$M^+$ in the aforementioned formula (I) preferably denotes an alkali metal cation or an ammonium ion.

$M^+$ more preferably denotes a potassium or a sodium ion, in particular preferably a sodium ion.

Anionic surfactants of the aforementioned formula (I) that are particularly preferred are the compounds known under the INCI names Sodium Cocoyl Methyl Isethionate, Potassium Cocoyl Methyl Isethionate, Ammonium Cocoyl Methyl Isethionate, Sodium Lauroyl Methyl Isethionate, Potassium Lauroyl Methyl Isethionate, Ammonium Lauroyl Methyl Isethionate, Sodium Myristoyl Methyl Isethionate, Potassium Myristoyl Methyl Isethionate and Ammonium Myristoyl Methyl Isethionate.

Sodium Cocoyl Methyl Isethionate and/or Sodium Lauroyl Methyl Isethionate are preferred in particular. Corresponding commercial products are available for example from Innospec under the commercial name "Iselux® LQ-CLR-SB".

The at least one anionic surfactant of the aforementioned formula (I) is preferably used in the mild cleansing agents according to the invention in an amount from 1.1 to 5 wt. %, more preferably from 1.2 to 4 wt. % and in particular from 1.25 to 3 wt. %, wherein the stated amounts relate to the total weight of the cleansing agent.

Suitable amphoteric and/or zwitterionic surfactants that can be used in the cleansing agents according to the invention preferably correspond to at least one compound of the following formulae (i) to (vii), in which the residue R denotes a straight-chain or branched, saturated or mono- or polyunsaturated alkyl or alkenyl residue having 7 to 23 carbon atoms (formulae (i) and (ii)) or a straight-chain or branched, saturated or mono- or polyunsaturated alkyl or alkenyl residue having 8 to 24 carbon atoms (formulae (iii) to (vii)):

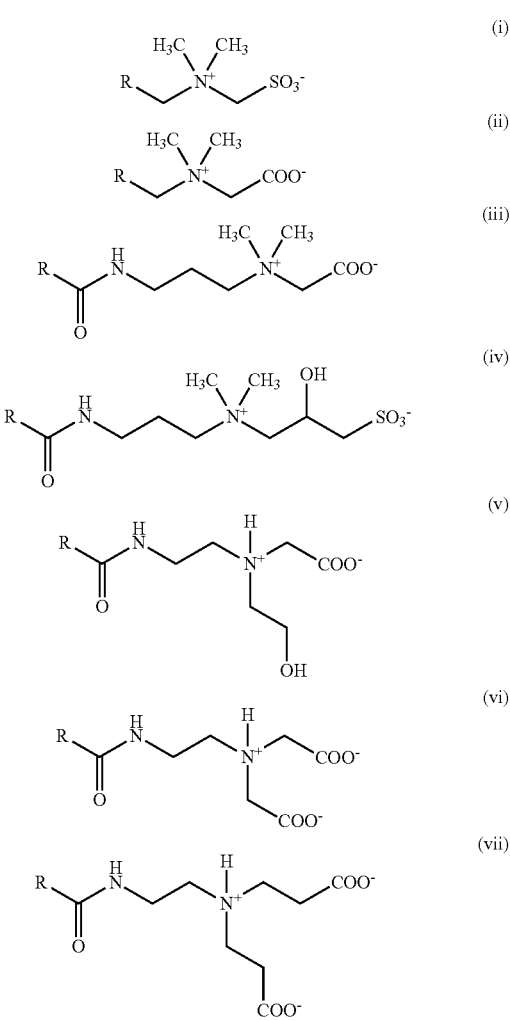

Preferred amphoteric and/or zwitterionic surfactants of one of the aforementioned formulae (i) to (vii) mostly include as the residue R a straight-chain or branched, saturated or mono- or polyunsaturated alkyl residue having 8 to 20, more preferably 8 to 16 and in particular 8 to 12 C atoms.

Amphoteric and/or zwitterionic surfactants in which the residue R is derived from coconut oil are more preferred.

Amphoteric and/or zwitterionic surfactants of formulae (iii), (v), (vi) and (vii) are more preferred.

The amphoteric surfactants known under the INCI names Cocamidopropyl Betaine and/or Cocoampho(di)acetate, which are commercially available from a number of suppliers, are preferred in particular.

The amphoteric/zwitterionic surfactant(s) of one of the aforementioned formulae (i) to (vii) can be used in the cleansing agents according to the invention—relative to the total weight thereof—in amounts preferably from 2.5 to 8.5 wt. %, preferably from 3 to 7.5 wt. % and in particular from 4 to 6 wt. %.

The suitable non-ionic surfactants and/or emulsifiers include
alkyl (oligo)glycosides,
amine oxides and/or
glycerol mono- and/or di($C_6$-$C_{24}$) carboxylic acid esters.

Suitable alkyl (oligo)glycosides can be selected from compounds of the general formula RO-$[G]_x$, in which [G] is preferably derived from aldoses and/or ketoses having 5-6 carbon atoms, preferably from glucose.

The index number x denotes the degree of oligomerization (DP), i.e. the distribution of mono- and oligoglycosides. The index number x preferably has a value in the range from 1 to 10, more preferably in the range from 1 to 3, wherein it need not be a whole number but can be a fraction which can be determined by analysis.

More preferred alkyl (oligo)glycosides have a degree of oligomerization between 1.2 and 1.5.

The residue R preferably denotes at least one alkyl and/or alkenyl residue having 4 to 24 C atoms.

Suitable amine oxides can be selected from at least one compound of the general formulae (II) or (III)

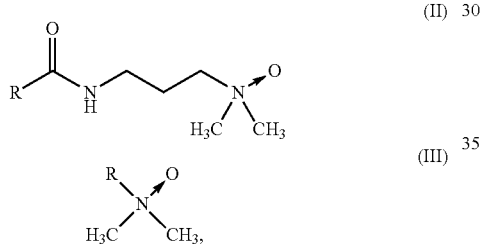

in which R in each case denotes a straight-chain or branched, saturated or mono- or polyunsaturated alkyl or alkenyl residue having 6 to 24 carbon atoms, preferably 8 to 18 carbon atoms.

The surfactants of the aforementioned formulae (II) or (III) that are known under the INCI names Cocamine Oxide, Lauramine Oxide and/or Cocamidopropylamine Oxide and are commercially available from a number of suppliers are preferred in particular.

Suitable glycerol mono- and/or di($C_6$-$C_{24}$) carboxylic acid esters are preferably understood to be a compound known under the INCI name Glyceryl Caprylate/Caprate.

The cosmetic cleansing agents more preferably include at least one alkyl (oligo)glycoside of the general formula RO-$[G]_x$, in which R denotes an alkyl and/or alkenyl residue having 4 to 22 C atoms, G denotes a sugar residue having 5 or 6 C atoms and x denotes numbers from 1 to 10, as the non-ionic surfactant and/or non-ionic emulsifier.

Alkyl (oligo)glycosides that are preferred in particular are the compounds known under the INCI names Caprylyl/Capryl Glucoside, Decyl Glucoside, Lauryl Glucoside and Coco Glucoside.

The non-ionic surfactant(s) and/or emulsifier(s) can be used in the cleansing agents according to the invention—relative to the total weight thereof—in amounts preferably from 0.75 to 8 wt. %, more preferably from 1 to 6 wt. % and in particular from 1.5 to 5 wt. %.

In a first more preferred embodiment mild cosmetic cleansing agents according to the invention include—relative to the total weight thereof—
a) 1.1 to 5 wt. % of at least one anionic surfactant of the aforementioned formula (I), in which the residue $R^1$ denotes a linear or branched, saturated or unsaturated alkyl residue having 8 to 18 carbon atoms, at least one of the residues $R^2$ to $R^5$ denotes a methyl residue and the other residues each denote a hydrogen atom, and $M^+$ denotes an alkali metal cation or an ammonium ion,
b) 2.5 to 8.5 wt. % of at least one amphoteric and/or zwitterionic surfactant of one of the aforementioned general formulae (iii), (v), (vi) or (vii), and
c) 0.75 to 8 wt. % of at least one non-ionic surfactant and/or non-ionic emulsifier of one of the aforementioned general formulae (II), (III) or RO-$[G]_x$.

Within this embodiment it is more preferable if the cleansing agents according to the invention include—relative to the total weight thereof—
a) 1.2 to 4 wt. % of at least one of the compounds known under the INCI names Sodium Cocoyl Methyl Isethionate, Potassium Cocoyl Methyl Isethionate, Ammonium Cocoyl Methyl Isethionate, Sodium Lauroyl Methyl Isethionate, Potassium Lauroyl Methyl Isethionate, Ammonium Lauroyl Methyl Isethionate, Sodium Myristoyl Methyl Isethionate, Potassium Myristoyl Methyl Isethionate and Ammonium Myristoyl Methyl Isethionate,
b) 3 to 7.5 wt. % of at least one of the amphoteric and/or zwitterionic surfactants known under the INCI names Cocamidopropyl Betaine and/or Cocoampho(di)acetate, and
c) 1 to 6 wt. % of at least one alkyl (oligo)glycoside of the general formula RO-$[G]_x$, in which R denotes an alkyl and/or alkenyl residue having 4 to 22 C atoms, G denotes a sugar residue having 5 or 6 C atoms and x denotes numbers from 1 to 10.

Mild cosmetic cleansing agents of this embodiment that are preferred in particular include—relative to the total weight thereof—
a) 1.25 to 3 wt. % of at least one of the compounds known under the INCI names Sodium Cocoyl Methyl Isethionate and/or Sodium Lauroyl Methyl Isethionate,
b) 4 to 6 wt. % of at least one amphoteric surfactant known under the INCI name Cocamidopropyl Betaine, and
c) 1.5 to 5 wt. % of at least one of the compounds known under the INCI names Caprylyl/Capryl Glucoside, Decyl Glucoside, Lauryl Glucoside and Coco Glucoside.

To further increase the care properties the mild cleansing agents according to the invention can moreover include at least one conditioning active ingredient, which can be selected from the group of
protein hydrolysates,
cationic polymers,
vitamins,
vegetable oils,
glycerol.

Suitable protein hydrolysates are understood to be mixtures of products which can be obtained by acidically, basically or enzymatically catalyzed breakdown of proteins.

Protein hydrolysates of plant, animal and/or marine origin can be used.

Animal protein hydrolysates are for example elastin, collagen, keratin, silk and milk protein hydrolysates, which can also be present in the form of salts. Such products are sold for example under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

Protein hydrolysates of plant origin, for example soy, almond, rice, pea, potato and wheat protein hydrolysates, are preferred. Such products are available for example under the trademarks Gluadin® (Cognis), DiaMin® (Diamalt), Lexein® (Inolex) and Crotein® (Croda).

Cationized protein hydrolysates can also be used, wherein the underlying protein hydrolysate can derive from animal sources, for example from collagen, milk or keratin, from plant sources, for example from wheat, maize, rice, potatoes, soy or almonds, from marine life forms, for example from fish collagen or algae, or from protein hydrolysates obtained by biotechnology. The protein hydrolysates underlying the cationic derivatives can be obtained from the corresponding proteins by means of a chemical, in particular alkaline or acid hydrolysis, an enzymatic hydrolysis and/or a combination of both types of hydrolysis. The hydrolysis of proteins generally gives rise to a protein hydrolysate having a molecular weight distribution from approximately 100 daltons to up to several thousand daltons. Cationic protein hydrolysates are preferred whose underlying protein component has a molecular weight of 100 to up to 25,000 daltons, preferably 250 to 5000 daltons. Cationic protein hydrolysates are moreover understood to include quaternized amino acids and mixtures thereof. The quaternization of the protein hydrolysates or the amino acids is frequently performed using quaternary ammonium salts such as for example N,N-dimethyl-N-(n-alkyl)-N-(2-hydroxy-3-chloro-n-propyl) ammonium halides. The cationic protein hydrolysates can moreover also be further derivatized. Typical examples of the cationic protein hydrolysates and derivatives are the commercially available products known under the following INCI names: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein.

The protein hydrolysate(s) can be used in the cleansing agents according to the invention—relative to the total weight thereof—in amounts preferably from 0.01 to 5 wt. %, more preferably from 0.025 to 3 wt. % and in particular from 0.05 to 2 wt. %.

Suitable cationic polymers are for example:
quaternized cellulose derivatives such as are available commercially under the names Celquat® and Polymer JR®,
hydrophobically modified cellulose derivatives, for example the cationic polymers sold under the trade name SoftCat®,
cationic alkyl polyglycosides,
cationized honey, for example the commercial product Honeyquat® 50,
cationic guar derivatives, such as in particular the products sold under the trade names Cosmedia® Guar N-Hance® and Jaguar®,
polymeric dimethyl diallyl ammonium salts and copolymers thereof with esters and amides of acrylic acid and methacrylic acid. The products available commercially under the names Merquat® 100 (poly(dimethyl diallyl ammonium chloride)) and Merquat® 550 (dimethyl diallyl ammonium chloride acrylamide copolymer) are examples of such cationic polymers,
copolymers of vinyl pyrrolidone with quaternized derivatives of dialkyl aminoalkyl acrylate and methacrylate, such as for example diethyl sulfate-quaternized vinyl pyrrolidone-dimethyl aminoethyl methacrylate copolymers. Such compounds are available commercially under the names Gafquat® 734 and Gafquat® 755,
vinyl pyrrolidone-vinyl imidazolium methochloride copolymers, such as are sold under the names Luviquat® FC 370, FC 550, FC 905 and HM 552,
quaternized polyvinyl alcohol,
as well as the polymers known under the names
Polyquaternium-2, Polyquaternium-17, Polyquaternium-18, Polyquaternium-24, Polyquaternium-27, Polyquaternium-32, Polyquaternium-37, Polyquaternium-74 and Polyquaternium-89.

Preferred cationic polymers are quaternized cellulose polymers, hydrophobically modified cationic cellulose derivatives, cationic guar derivatives and/or cationic polymers based on acrylic acid (derivatives), which are more preferably selected from the polymers known under the INCI names Guar Hydroxypropyltrimonium Chloride, Polyquaternium-6, Polyquaternium-7, Polyquaternium-10, Polyquaternium-37 and/or Polyquaternium-67.

The polymers known under the INCI names Guar Hydroxypropyltrimonium Chloride, Polyquaternium-10 and/or Polyquaternium-67 are preferred in particular.

The cationic polymer(s) can be used in the cleansing agents according to the invention—relative to the total weight thereof—in an amount preferably from 0.01 to 5 wt. %, more preferably from 0.025 to 4 wt. %, more preferably from 0.05 to 3 wt. % and in particular from 0.1 to 2 wt. %.

Suitable vitamins are understood to be preferably the following vitamins, provitamins and vitamin precursors as well as derivatives thereof:

Vitamin A: The group of substances classed as vitamin A includes retinol (vitamin $A_1$) and 3,4-didehydroretinol (vitamin $A_2$). β-Carotene is the retinol provitamin. Suitable vitamin A components are for example vitamin A acid and esters thereof, vitamin A aldehyde and vitamin A alcohol and esters thereof such as the palmitate and acetate.

Vitamin B: The vitamin B group or vitamin B complex includes inter alia

Vitamin $B_1$ (thiamine)

Vitamin $B_2$ (riboflavin)

Vitamin $B_3$. The compounds nicotinic acid and nicotinic acid amide (niacinamide) are often included under this term.

Vitamin $B_5$ (pantothenic acid and panthenol). Within this group panthenol is preferably used. Derivatives of panthenol which can be used are in particular the esters and ethers of panthenol, pantolactone as well as cationically derivatized panthenols. Individual representatives are for example panthenol triacetate, panthenol monoethyl ether and the monoacetate thereof, and cationic panthenol derivatives.

Vitamin $B_6$ (pyridoxine as well as pyridoxamine and pyridoxal).

Vitamin C (ascorbic acid): Use in the form of the palmitic acid ester, glucosides or phosphates can be preferred. Use in combination with tocopherols can likewise be preferred.

Vitamin E (tocopherols, in particular α-tocopherol).

Vitamin F: The term "vitamin F" is conventionally understood to mean essential fatty acids, in particular linoleic acid, linolenic acid and arachidonic acid.

Vitamin H: Vitamin H is the name given to the compound (3aS,4S,6aR)-2-oxohexahydrothienol[3,4-d]-imidazole-4-valeric acid, although this is now more widely known by the trivial name biotin.

The cleansing agents according to the invention can preferably include vitamins, provitamins and vitamin precursors from groups A, B, E and H.

Nicotinic acid amide, biotin, pantolactone and/or panthenol are preferred in particular.

Vitamins, vitamin derivatives and/or vitamin precursors can be used in the cleansing agents according to the invention—relative to the total weight thereof—in an amount preferably from 0.001 to 2 wt. %, more preferably from 0.005 to 1 wt. % and in particular from 0.01 to 0.5 wt. %.

Suitable natural (vegetable) oils are conventionally understood to be triglycerides and mixtures of triglycerides. Preferred natural oils are coconut oil, (sweet) almond oil, walnut oil, peach kernel oil, apricot kernel oil, avocado oil, tea tree oil, soybean oil, sesame oil, sunflower oil, tsubaki oil, evening primrose oil, rice bran oil, palm kernel oil, mango kernel oil, lady's smock oil, thistle oil, macadamia nut oil, grape seed oil, amaranth seed oil, argan oil, bamboo oil, olive oil, wheatgerm oil, pumpkin seed oil, mallow oil, hazelnut oil, safflower oil, canola oil, sasanqua oil, jojoba oil, rambutan oil, cocoa butter and/or shea butter.

Vegetable oils can be used in the cleansing agents according to the invention in amounts preferably from 0.01 to 5 wt. %, more preferably from 0.025 to 4 wt. %, more preferably from 0.05 to 3 wt. % and in particular from 0.1 to 2 wt. %, the stated amounts relating to the total weight of the cleansing agents.

Glycerol can be added separately to the cleansing agents according to the invention in an amount of up to 10 wt. % (relative to the total weight of the cleansing agent). It can however also be a constituent of the aqueous-alcoholic carrier.

In a second more preferred embodiment mild cosmetic cleansing agents according to the invention include—relative to the total weight thereof— a) 1.1 to 5 wt. % of at least one anionic surfactant of the aforementioned formula (I), in which the residue $R^1$ denotes a linear or branched, saturated or unsaturated alkyl residue having 8 to 18 carbon atoms, at least one of the residues $R^2$ to $R^5$ denotes a methyl residue and the other residues each denote a hydrogen atom, and $M^+$ denotes an alkali metal cation or an ammonium ion, b) 2.5 to 8.5 wt. % of at least one amphoteric and/or zwitterionic surfactant of one of the aforementioned general formulae (iii), (v), (vi) or (vii), c) 0.75 to 8 wt. % of at least one non-ionic surfactant and/or non-ionic emulsifier of one of the aforementioned general formulae (II), (III) or RO-$[G]_x$, and d) at least one conditioning active ingredient selected from the group of protein hydrolysates, cationic polymers, vitamins, vegetable oils and glycerol.

Within this embodiment it is more preferable if the cleansing agents according to the invention include—relative to the total weight thereof— a) 1.2 to 4 wt. % of at least one of the compounds known under the INCI names Sodium Cocoyl Methyl Isethionate, Potassium Cocoyl Methyl Isethionate, Ammonium Cocoyl Methyl Isethionate, Sodium Lauroyl Methyl Isethionate, Potassium Lauroyl Methyl Isethionate, Ammonium Lauroyl Methyl Isethionate, Sodium Myristoyl Methyl Isethionate, Potassium Myristoyl Methyl Isethionate and Ammonium Myristoyl Methyl Isethionate, b) 3 to 7.5 wt. % of at least one of the amphoteric and/or zwitterionic surfactants known under the INCI names Cocamidopropyl Betaine and/or Cocoamphodiacetate, c) 1 to 6 wt. % of at least one alkyl (oligo)glycoside of the general formula RO-$[G]_x$, in which R denotes an alkyl and/or alkenyl residue having 4 to 22 C atoms, G denotes a sugar residue having 5 or 6 C atoms and x denotes numbers from 1 to 10, and d) at least one cationic polymer selected from cationic cellulose derivatives, hydrophobically modified cationic cellulose derivatives, cationic guar derivatives and/or glycerol.

Mild cosmetic cleansing agents of this embodiment that are preferred in particular include—relative to the total weight thereof— a) 1.25 to 3 wt. % of at least one of the compounds known under the INCI names Sodium Cocoyl Methyl Isethionate and/or Sodium Lauroyl Methyl Isethionate, b) 4 to 6 wt. % of at least one amphoteric surfactant known under the INCI name Cocamidopropyl Betaine, c) 1.5 to 5 wt. % of at least one of the compounds known under the INCI names Caprylyl/Capryl Glucoside, Decyl Glucoside, Lauryl Glucoside and Coco Glucoside, and d) at least one of the cationic polymers known under the INCI names Guar Hydroxypropyltrimonium Chloride, Polyquaternium-10 and/or Polyquaternium-67 and glycerol.

As has already been stated, the mild cleansing agents according to the invention are suitable as skin and/or hair cleansing agents for babies and small children.

For such application forms it is advantageous for the cleansing agents additionally to include a bitter principle which has a molar mass of at least 250 g/mol and which is soluble up to at least 10 mg/l in the cleansing agent at 20° C.

Examples of suitable bitter principles are quaternary ammonium compounds including an aromatic group in both the cation and the anion. Such compounds are commercially available, for example under the trademarks Bitrex® and Indigestin® (benzyldiethyl((2,6-xylylcarbamoyl)methyl) ammoniumbenzoate) or under the name Denatonium Benzoate.

The bitter principle(s) can be included in the compositions according to the invention preferably in amounts from 0.0005 to 0.1 wt. %, relative to the total preparation. Amounts from 0.001 to 0.05 wt. % are more preferred.

From an ecological perspective it is moreover preferable for cleansing agents according to the invention to be substantially free from ethoxylated active ingredients.

In particular, if cleansing agents according to the invention are to be presented as skin and/or hair cleansing agents for babies and small children, then it is preferable for the cleansing agents to be substantially free from ethoxylated active ingredients.

"Substantially free from ethoxylated active ingredients" is understood to mean that the cleansing agents according to the invention include preferably less than 0.5 wt. %, more preferably less than 0.25 wt. % and in particular less than 0.1 wt. % of ethoxylated active ingredients.

"Ethoxylated active ingredients" are preferably understood to be active ingredients comprising the following groupings:

$$H-(O-CH_2CH_2)_n-OH, \quad\quad 1)$$

in which n denotes whole numbers between 1 and 100,000,

$$H-(O-CH(CH_3)CH_2)_n-OH, \quad\quad 2)$$

in which n denotes whole numbers between 1 and 100,000,

$$R-(O-CH_2CH_2)_n-OH, \quad\quad 3)$$

in which R denotes an alkyl or alkenyl residue having 2 to 30 C atoms and n denotes numbers between 1 and 10,000,

$$R-(O-CH_2CH_2)_n-OSO_3H, \quad\quad 4)$$

in which R denotes an alkyl or alkenyl residue having 2 to 30 C atoms and n denotes numbers between 1 and 10,000, and

$$-(O-CH_2CH_2)_n-, \quad\quad 5)$$

in which n denotes whole numbers between 2 and 100,000.

The agents according to the invention are preferably free from polyethylene glycols of the general formula 1), i.e. they preferably include neither ethylene glycol (n=1) nor products having a degree of polymerization $P_n$=2-4 (diethylene glycol, triethylene glycol and tetraethylene glycol) nor polyethylene glycols having higher degrees of polymerization $P_n$ from approx. 5 to 100,000, which can no longer be produced such that they are monodisperse but are instead polydisperse.

They are preferably also free from polypropylene glycols of the general formula 2), i.e. they include neither propylene glycol (n=1) nor products having a degree of polymerization $P_n$=2-4 (dipropylene glycol, tripropylene glycol and tetrapropylene glycol) nor polypropylene glycols having higher degrees of polymerization $P_n$ from approx. 5 to 100,000, which can no longer be produced such that they are monodisperse but are instead polydisperse.

It has been found that the use of other ethoxylated compounds should preferably also be avoided. In particular, nonionic surfactants of the alkyl or alkenyl ethoxylate type likewise reduce the positive effects of the agents according to the invention and should therefore not be used in the cleansing agents according to the invention. Thus cleansing agents that are preferred according to the invention also include no compounds of formula 3).

Agents according to the invention that are substantially free from alkyl ether sulfates of the aforementioned formula 4) are moreover preferred, wherein "substantially free" is understood to have the meaning defined above.

In more preferred agents according to the invention the use of compounds having ethoxylated groupings is avoided entirely.

Preferred cleansing agents according to the invention thus include no compound including the grouping $-(O-CH_2CH_2)_n-O-$ with n=1 to 10,000. More preferred skin and/or hair cleansing agents according to the invention are therefore characterized in that they include no compounds of formula 5).

A sensitive scalp can be caused by the occurrence of dandruff and the associated itching. It must be treated with especially mild cleansing compositions which effectively and lastingly remove dandruff and care for the scalp without subjecting it to additional stress.

It has been found that cleansing agents according to the invention are also suitable for an application as an anti-dandruff cleansing preparation.

For the presentation form as an anti-dandruff agent, agents according to the invention include—relative to the total weight thereof—preferably 0.01 to 10 wt. %, more preferably 0.025 to 7.5 wt. %, more preferably 0.05 to 5 wt. % and in particular 0.075 to 3 wt. % of at least one anti-dandruff active ingredient.

Suitable anti-dandruff active ingredients can be selected from piroctone olamine, climbazole, zinc pyrithione, ketoconazoles, salicylic acid, sulfur, selenium sulfide, tar preparations, undecenoic acid derivatives, burdock extracts, poplar extracts, stinging nettle extracts, walnut shell extracts, birch extracts, willow bark extracts, rosemary extracts and/or arnica extracts.

Climbazole, zinc pyrithione and piroctone olamine are preferred.

Further active ingredients, auxiliary substances and additives that can be included in the cleansing agents according to the invention are for example:

plant extracts,
humectants,
perfumes,
UV filters,
thickening agents such as gelatins or plant gums, for example agar-agar, guar gum, alginates, xanthan gum, gum arabic, karaya gum, carob seed meal, linseed gums, dextrans, cellulose derivatives, for example methyl cellulose, hydroxyalkyl cellulose and carboxymethyl cellulose, starch fractions and derivatives such as amylose, amylopectin and dextrins, clays and phyllosilicates such as for example bentonite or fully synthetic hydrocolloids such as for example polyvinyl alcohol, the Ca, Mg or Zn soaps,
texturizing agents such as maleic acid and lactic acid,
dimethyl isosorbide,
cyclodextrins,
active ingredients to improve the fiber structure, in particular mono-, di- and oligosaccharides such as for example glucose, galactose, fructose, fruit sugar and lactose,
dyes to color the agent,
substances to adjust the pH, for example α- and β-hydroxycarboxylic acids such as citric acid, lactic acid, malic acid, glycolic acid, active ingredients such as bisabolol,
complexing agents such as EDTA, NTA, β-alanine diacetic acid and phosphonic acids,
ceramides. Ceramides are understood to be N-acyl sphingosine (fatty acid amides of sphingosine) or synthetic analogs of such lipids (known as pseudoceramides),
propellants such as propane-butane mixtures, $N_2O$, dimethyl ether, $CO_2$ and air,
antioxidants,
preservatives, such as for example sodium benzoate or salicylic acid,
viscosity adjusters such as salts (NaCl).

The mild cleansing agents according to the invention preferably have a pH in the range from 3 to 6, more preferably from 3.5 to 6, more preferably from 4 to 5.5 and in particular from 4.5 to 5.5.

The cleansing agents according to the invention have the advantage that they are particularly mild and well tolerated by the skin.

They also exhibit an excellent care performance, in particular when the cleansing agents are applied to the hair. An addition of silicones is unnecessary.

All raw materials that are needed for the formulation can be dissolved in the cosmetic carrier, preferably in water, which means that the addition of ethoxylated solubilizers is likewise unnecessary.

The cleansing agents according to the invention are extremely highly foaming and yield a dense foam that is easy to distribute over the application surface. The use of sulfate surfactants can thus be avoided.

The cleansing agents according to the invention have an excellent texture and are free-flowing.

It is moreover advantageous that the cleansing agents according to the invention are stable even at relatively low pH values. This allows a well-tolerated acid preservation of the agents.

The invention secondly provides the use of the mild cosmetic cleansing agents according to the invention as sensitive facial cleansing agents, as a baby shampoo and/or as a baby bath preparation.

EXAMPLES

1) Formulation Examples

The following cleansing agents according to the invention were prepared (unless otherwise specified, the stated amounts relate to percentages by weight):

TABLE 1

|  | Baby shampoo 1 | Kids' shampoo 2 |
|---|---|---|
| Iselux ®[1] LQ-CLR-SB | 5 | 5 |
| Coco-Glucoside (50% AS) | 7 | 4 |
| Cocamidopropyl Betaine (40% AS) | 13 | 13 |
| Polyquaternium-10 | 0.1 |  |
| Polyquaternium-67 |  | 0.3 |
| Glycerol | 5 | 5 |
| Panthenol | 0.2 |  |
| Bitrex ®[2] |  | 0.08 |
| Acidulants, preservatives | qs | qs |
| Water | to 100 | to 100 |

The following commercial products were used in the cleansing agents of Table 1:
[1]INCI name: Sodium Lauroyl Methyl Isethionate; 32% AS; Innospec
[2]INCI name: Water, Denatonium Benzoate; 2.5% AS; Macfarlan Smith Ltd.

Cleansing agents 1 and 2 are especially mild, caring and have only a very slight skin-irritating effect.

2) Assessment of the Formulation Examples

Cleansing agents 1 and 2 were compared in a test (reaction time method) with various commercially available baby and children's shampoos. The shampoos were diluted down to 50% with water in each case.
A 5% sodium laureth sulfate solution served as a reference.
A Q value of >1.20 denotes an irritating effect; a Q value of <0.8 denotes slight irritation.

The results of the test are shown in Table 2 below:

TABLE 2

|  | Concentration (in water) | pH | Reaction time method [Q] | Evaluation |
|---|---|---|---|---|
| Baby shampoo 1 | 50% | 4.8 | 0.36 | slightly irritating |
| Kids' shampoo 2 | 50% | 4.9 | 0.37 | slightly irritating |
| Bubchen baby shampoo | 50% | 7.3 | 0.42 | slightly irritating |
| Bubchen children's shampoo | 50% | 5.7 | 0.59 | slightly irritating |
| Bubchen kids' shampoo | 50% | 5.7 | 1.23 | irritating |
| Penaten baby bath & shampoo | 50% | 5.8 | 0.43 | slightly irritating |
| Reference (SLES, 5% in water) | 5% | 7.2 | 1.00 | moderately irritating |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A mild cosmetic cleansing agent, including in a suitable carrier
a) 1 to 6 wt. % of at least one anionic surfactant of following formula (I), $$R^1-\overset{O}{\underset{}{\|}}-O-\overset{R^2}{\underset{R^3}{\vphantom{|}}}\overset{R^4}{\underset{R^5}{\vphantom{|}}}-SO_3^-M^+ \quad (I)$$

in which
$R^1$ denotes a linear or branched, saturated or unsaturated alkyl residue having 6 to 30 carbon atoms,
at least one of the residues $R^2$ to $R^5$ denotes a $C_1$-$C_4$ alkyl residue, and the other residues among $R^2$ to $R^5$ independently of one another denote a hydrogen atom or a $C_1$-$C_4$ alkyl residue, and
$M^+$ denotes an ammonium, alkanolammonium or metal cation, b) 2 to 10 wt. % of at least one amphoteric and/or zwitterionic surfactant and c) 0.5 to 10 wt. % of at least one non-ionic surfactant and/or at least one non-ionic emulsifier, selected from the group consisting of alkyl (oligo)glycosides, amine oxides, and glycerol mono- and/or di($C_6$-$C_{24}$) carboxylic acid esters, wherein the surfactants/emulsifiers a), b) and c) are included in a weight ratio of 1:(3.25-5):(1-3), the cleansing agent is substantially free from ethoxylated active ingredients, and wherein the stated amounts relate to the total weight of the cleansing agent.

2. The mild cosmetic cleansing agent according to claim 1, wherein the anionic surfactant according to formula (I) is characterized such that $R^1$ denotes a linear or branched, saturated or unsaturated alkyl residue having 8 to 18 carbon atoms, and at least one of the residues $R^2$ to $R^5$ denotes a methyl residue, and the other residues denote a hydrogen atom.

3. The mild cosmetic cleansing agent according claim 1, wherein the anionic surfactant according to formula (I) is characterized such that $R^1$ denotes a $C_8$, $C_{10}$, $C_{12}$, $C_{14}$, $C_{16}$ residue or mixtures of these fatty acid residues, such as are obtained when the fatty acid(s) is/are derived from natural oils such as for example coconut oil, and one of the residues $R^2$ to $R^5$ denotes a methyl residue, and the other residues denote a hydrogen atom.

4. The mild cosmetic cleansing agent according to claim 1, farther comprising at least one compound of the following formulae (i) to (vii), in which the residue R denotes a straight-chain or branched, saturated or mono or polyunsaturated alkyl or alkenyl residue having 7 to 23 carbon atoms (formulae (i) and (ii)) or a straight-chain or branched, saturated or mono- or polyunsaturated alkyl or alkenyl residue having 8 to 24 carbon atoms (formulae (iii) to (vii)):

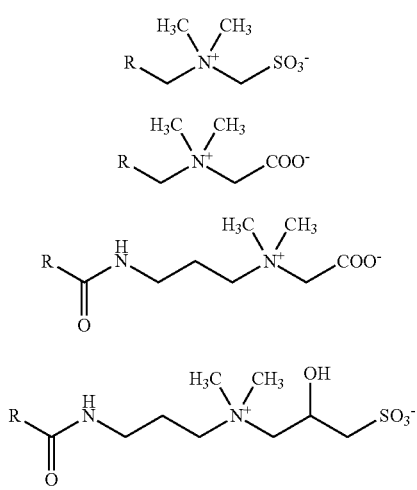

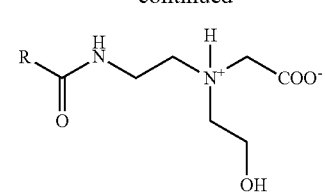

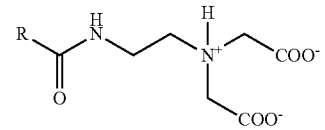

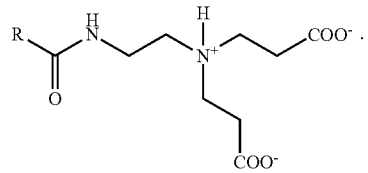

5. The mild cosmetic cleansing agent according to claim 4, Wherein the amphoteric and/or zwitterionic surfactants of formulae (iii), (v), (vi) and (vii) are included, in which the residue R is derived from coconut oil.

6. The mild cosmetic cleansing agent according to claim 1, wherein the non-ionic surfactant and/or non-ionic emulsifier includes at least one alkyl (oligo)glycoside of the general formula RO-[G]$_x$, in which R denotes an alkyl and/or alkenyl residue having 4 to 22 C atoms, G denotes a sugar residue having 5 or 6 C atoms and x denotes numbers from 1 to 10, and/or at least one amine oxide of one of the following formulae (II) or (III),

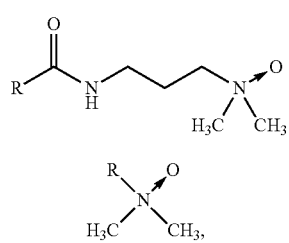

in which R in each case denotes a straight-chain or branched, saturated or mono- or polyunsaturated alkyl or alkenyl residue having 6 to 24 carbon atoms, preferably 8 to 18 carbon atoms.

7. The mild cosmetic cleansing agent according to claim 4, wherein the agent includes, relative to its total weight, a) 1.1 to 5 wt. % of at least one anionic surfactant of the aforementioned formula (I), in which the residue $R^1$ denotes a linear or branched, saturated or unsaturated alkyl residue having 8 to 18 carbon atoms, at least one of the residues $R^2$ to $R^5$ denotes a methyl residue and the other residues each denote a hydrogen atom, and $M^+$ denotes an alkali metal cation or an ammonium ion, b) 2.5 to 8.5 wt % of at least one amphoteric and/or zwitterionic surfactant of one of the aforementioned general formulae (iii), (v), (vi) or (vii), and c) 0.75 to 8 wt % of the at least one non-ionic surfactant and/or non-ionic emulsifier, being selected from the group consisting of formula (II), formula (III) or formula RO-[G]$_x$ in which R denotes an alkyl and/or alkenyl residue having 4 to 22 C atoms, G denotes a sugar residue having 5 or 6 C atoms and x denotes numbers from 1 to 10

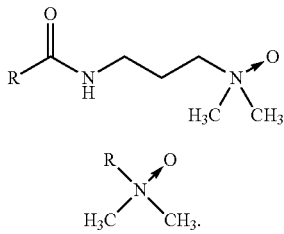

8. The mild cosmetic cleansing agent according to claim 1, further comprising at least one conditioning active ingredient selected from the group consisting of
   protein hydrolysates,
   cationic polymers,
   vitamins,
   vegetable oils
   glycerol.

9. The mild cosmetic cleansing agent according to claim 8, including at least one cationic polymer, being selected from the group consisting of cationic cellulose derivatives, hydrophobically modified cationic cellulose derivatives, cationic guar derivatives, and glycerol.

10. The mild cosmetic cleansing agent according to claim 1, further comprising at least one bitter principle having a molar mass of at least 250 g/mol and being soluble up to at least 10 mg/l in the cleansing agent at 20° C.

11. The mild cosmetic cleansing agent according to claim 4, wherein the agent includes, relative to its total weight,
   a) 1.1 to 5 wt. % of at least one anionic surfactant of the aforementioned formula (I), in which the residue R$^1$ denotes a linear or branched, saturated or unsaturated alkyl residue having 8 to 18 carbon atoms, at least one of the residues R$^2$ to R$^5$ denotes a methyl residue and the other residues each denote a hydrogen atom, and M$^+$ denotes an alkali metal cation or an ammonium ion,
   b) 2.5 to 8.5 wt. % of at least one amphoteric and/or zwitterionic surfactant of one of the aforementioned general formulae (iii), (v), (vi) or (vii),
   c) 00.75 to 8 wt. % of the at least one non-ionic surfactant and/or non-ionic emulsifier, being selected from the group consisting of formula (II), formula (III) or formula RO-[G]$_x$ in which R denotes an alkyl and/or alkenyl residue having 4 to 22 C atoms, G denotes a sugar residue having 5 or 6 C atoms and x denotes numbers from 1 to 10

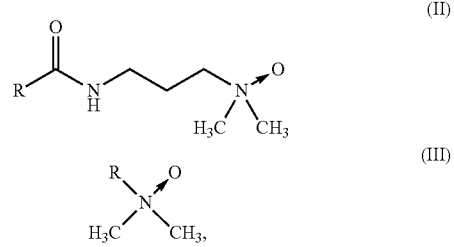

d) at least one conditioning active ingredient selected from the group of protein hydrolysates, cationic polymers, vitamins, vegetable oils and glycerol, and
   e) at least one bitter principle which has a molar mass of at least 250 g/mol and which is soluble up to at least 10 mg/l in the cleansing agent at 20° C.

12. The mild cosmetic cleansing agent according to claim 1, wherein the agent has a pH in the range from 4 to 5.5.

\* \* \* \* \*